(12) United States Patent
Zapf et al.

(10) Patent No.: US 7,589,081 B2
(45) Date of Patent: Sep. 15, 2009

(54) NITROGEN-CONTAINING MONODENTATE PHOSPHINES AND THEIR USE IN CATALYSIS

(75) Inventors: Alexander Zapf, Rostock (DE); Mark Sundermeier, Zürich (CH); Ralf Jackstell, Cuxhaven (DE); Matthias Beller, OB Nienhagen (DE); Thomas Riermeier, Flörsheim (DE); Axel Monsees, Frankfurt (DE); Uwe Dingerdissen, Seeheim (DE)

(73) Assignee: DEGUSSA GmbH, Duesseldorf (DE)

( * ) Notice: Subject to any disclaimer, the term of this patent is extended or adjusted under 35 U.S.C. 154(b) by 619 days.

(21) Appl. No.: 10/554,603

(22) PCT Filed: May 3, 2004

(86) PCT No.: PCT/EP2004/004644

§ 371 (c)(1),
(2), (4) Date: Oct. 27, 2005

(87) PCT Pub. No.: WO2004/101581

PCT Pub. Date: Nov. 25, 2004

(65) Prior Publication Data

US 2007/0123707 A1     May 31, 2007

(30) Foreign Application Priority Data

May 16, 2003   (DE) ................... 103 22 408

(51) Int. Cl.
*A61K 31/675*   (2006.01)
*C07F 9/28*   (2006.01)

(52) U.S. Cl. .............. 514/89; 514/91; 546/22; 548/111; 548/412

(58) Field of Classification Search ............ 546/22; 548/111, 412; 514/89, 91
See application file for complete search history.

(56) References Cited

FOREIGN PATENT DOCUMENTS

WO        02/055528        7/2002

OTHER PUBLICATIONS

Chevykalova, M. N. et al "Electron-donating ability of triarylphosphines and related compunds studied by 31P NMR spectroscopy", Russian Chemical Bulletin, vol. 52, No. 1, pp. 78-84, 2003.*

Zapf, Alexander et al: "Practical synthesis of new and highly efficient ligands for the Suzuki reaction of aryl chlorides", Chemical Communications, pp. 38-39, 2004.*

Drexler, Hans-Joachim et al: "Part III. COD versus NBD precatalysts. Dramatic difference in the asymmetric hydrogenation of prochiral olefins with five-membered diphosphine Rh-hydrogenation catalysts", Journal of Organometallic Chemistry, vol. 621, No. 1-2, pp. 89-102, 2001.

Wolfe, John P. et al: "A Highly Active Catalyst for the Room-Temperature Amination and Suzuki Coupling of Aryl Chlorides", Angewandte Chemie. International Edition, vol. 38, No. 16, pp. 2413-2416, 1999.

* cited by examiner

*Primary Examiner*—Rei-Tsang Shiao
*Assistant Examiner*—Janet L Coppins
(74) *Attorney, Agent, or Firm*—Oblon, Spivak, McClelland, Maier & Neustadt, P.C.

(57) ABSTRACT

The present invention relates to novel nitrogen-containing monodentate phosphane ligands of formula (I) and to their use in catalytic reactions, especially in the improvement of haloaromatic compounds.

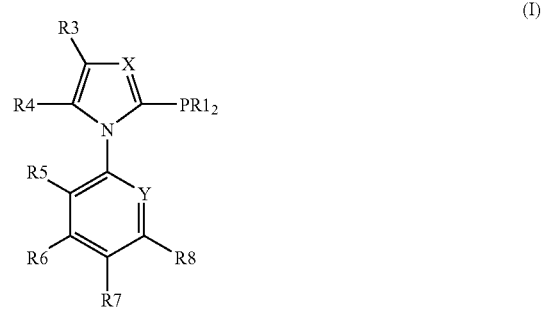

18 Claims, No Drawings

NITROGEN-CONTAINING MONODENTATE PHOSPHINES AND THEIR USE IN CATALYSIS

The present invention relates to novel ligands for transition metals, to their preparation and to their use in catalytic reactions, especially for the improvement of haloaromatic compounds.

Haloaromatic compounds, including especially chloroaromatic compounds, are intermediates which can be used variously in the chemical industry and which serve as preliminary products for the production of agricultural intermediates, pharmaceuticals, colourings, materials, etc. Vinyl halides are also important intermediates which are used as starting materials for polymers and in the production of the above-mentioned products.

Catalysts which are frequently employed for the functionalisation of haloaromatic compounds or vinyl halides to aromatic olefins or dienes (Heck reaction, Stille reaction), biaryls (Suzuki reaction), alkynes (Sonogashira reaction), carboxylic acid derivatives (Heck carbonylation), amines (Buchwald-Hartwig reaction) are palladium catalysts and nickel catalysts. Palladium catalysts are generally advantageous, owing to the wide applicability of coupling substrates with in some cases good catalytic activities, while nickel catalysts have advantages in the field of the reaction of chloroaromatic compounds and vinyl chlorides. Moreover, nickel is more readily available than palladium.

Palladium and nickel catalysts used within the scope of the activation and further improvement of haloaromatic compounds are both palladium(II) and/or nickel(II) complexes as well as palladium(0) and/or nickel(0) complexes, although it is known that palladium(0) and nickel(0) compounds are the actual catalysts of the reaction. In particular, according to information in the literature, coordinatively-unsaturated 14- and 16-electron palladium(0) and nickel(0) complexes stabilised with donor ligands such as phosphanes are formulated as the active species.

When iodides are used as starting materials in coupling reactions it is also possible to dispense with phosphane ligands. However, aryl iodides and vinyl iodides are starting materials which are scarcely available and therefore very expensive, and their reaction additionally yields stoichiometric amounts of iodine salt waste products. If other starting materials are used in the Heck reaction, such as aryl bromides or aryl chlorides, the addition of stabilising and activating ligands is necessary if catalytically effective reaction of the starting materials is to be possible.

The catalyst systems described for olefinations, alkynylations, carbonylations, arylations, aminations and similar reactions frequently have satisfactory catalytic turnover numbers (TON) only with uneconomical starting materials such as iodoaromatic compounds and activated bromoaromatic compounds. Otherwise, in the case of deactivated bromoaromatic compounds and, especially, in the case of chloroaromatic compounds, large amounts of catalyst—usually more than 1 mol. %—must generally be added in order to achieve industrially usable yields (>90%). Moreover, owing to the complexity of the reaction mixtures, simple recycling of the catalyst is not possible, so that recovery of the catalyst also gives rise to high costs, which generally stand in the way of industrial implementation. Furthermore, it is undesirable to work with large amounts of catalyst, especially when preparing active ingredients or preliminary products for active ingredients, because catalyst residues otherwise remain in the product in this case.

More recent active catalyst systems are based on cyclopalladated phosphanes (W. A. Herrmann, C. BroBmer, K. Öfele, C.-P. Reisinger, T. Priermeier, M. Beller, H. Fischer, *Angew. Chem.* 1995, 107, 1989; *Angew. Chem. Int. Ed. Engl.* 1995, 34, 1844) or mixtures of sterically demanding arylphosphanes (J. P. Wolfe, S. L. Buchwald, *Angew. Chem.* 1999, 111, 2570; *Angew. Chem. Int. Ed. Engl.* 1999, 38, 2413) or tri-tert.-butylphosphane (A. F. Littke, G. C. Fu, *Angew. Chem.* 1998, 110, 3586; *Angew. Chem. Int. Ed. Engl.* 1998, 37, 3387) with palladium salts or palladium. complexes.

However, chloroaromatic compounds can generally not be activated in an industrially satisfactory manner even using these catalysts. Accordingly, in order to achieve high yields, comparatively large, amounts of catalyst must be used. Therefore, despite all the further developments which have been made to catalysts in recent years, only a small number of industrial reactions of the arylation, carbonylation, olefination, etc. of chloroaromatic compounds have hitherto become known.

For the mentioned reasons, the object underlying the present invention was to provide novel ligands and catalysts which are suitable for large-scale applications, are readily accessible and convert chloro- and bromo-aromatic compounds as well as corresponding vinyl compounds to the respective coupling products in high yield and with high purity, with high catalyst productivity.

This object is achieved according to the invention by novel phosphane ligands of formula (I)

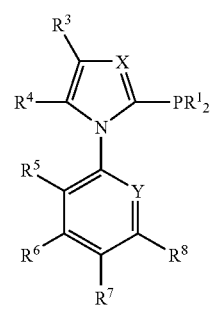

wherein
X independently of Y represents a nitrogen atom or a C—R² group and
Y independently of X represents a nitrogen atom or a C—R⁹ group,
R¹ for each of the two R¹ groups independently of the other represents a radical selected from the group $C_1$-$C_{24}$-alkyl,
  $C_3$-$C_{20}$-cycloalkyl, which includes especially both monocyclic and also bi- and tri-cyclic cycloalkyl radicals,
  $C_5$-$C_{14}$-aryl, which includes especially the phenyl, naphthyl, fluorenyl radical,
  $C_2$-$C_{13}$-heteroaryl, wherein the number of hetero atoms, selected from the group N, O, S, may be from 1 to 2,
  wherein the two radicals R¹ may also be linked to one another, there preferably being formed a 4- to 8-membered saturated, unsaturated or aromatic ring.

The above-mentioned radicals R¹ may themselves each be mono- or poly-substituted. These substituents, independently of one another, may be hydrogen, $C_1$-$C_{20}$-alkyl, $C_2$-$C_{20}$-alkenyl, $C_3$-$C_8$-cycloalkyl, $C_2$-$C_9$-hetero-alkyl $C_5$-$C_{10}$-aryl, $C_2$-$C_9$-heteroaryl, wherein the number of hetero atoms, especially from the group N, O, S, may be from 1 to 4, $C_1$-$C_{20}$-alkoxy, preferably $C_1$-$C_{10}$-alkoxy, particularly preferably OMe, $C_1$-$C_{10}$-halo-alkyl, preferably trifluoromethyl, hydroxy, secondary, tertiary amino groups of the forms NH—($C_1$-$C_{20}$-alkyl), NH—($C_5$-$C_{10}$-aryl), N($C_1$-$C_{20}$-alkyl)$_2$, N($C_1$-$C_{20}$-alkyl) ($C_5$-$C_{10}$-aryl), N($C_5$-$C_{10}$-aryl)$_2$, N($C_1$-$C_{20}$-alkyl/$C_5$-$C_{10}$-aryl)$_3$$^+$, NH—CO—$C_1$-$C_{20}$-alkyl, NH—CO—$C_5$-$C_{10}$-aryl, carboxylato of the forms COOH and COOQ (wherein Q represents either a monovalent cation or $C_1$-$C_8$-alkyl), $C_1$-$C_6$-acyloxy, sulfinato, sulfonato of the forms $SO_3H$ and $SO_3Q$ (wherein Q represents either a monovalent cation, $C_1$-$C_{20}$-alkyl or $C_5$-$C_{10}$-aryl) tri-$C_1$-$C_6$-alkylsilyl, especially $SiMe_3$, wherein two of the mentioned substituents may also be bridged with one another, there preferably being formed a 4- to 8-membered ring which can be further substituted preferably by linear or branched $C_1$-$C_{10}$-alkyl, $C_6$-aryl, benzyl, $C_1$-$C_{10}$-alkoxy, hydroxy or benzyloxy groups.

$R^2$-$R^9$ represent a hydrogen, alkyl, alkenyl, cycloalkyl, aromatic or heteroaromatic aryl, O-alkyl, NH-alkyl, N-(alkyl)$_2$, O-(aryl), NH-(aryl), N-(alkyl) (aryl), O—CO -alkyl, O—CO-aryl, F, Si(alkyl)$_3$, $CF_3$, CN, $CO_2H$, COH, $SO_3H$, $CONH_2$, CONH(alkyl), CON(alkyl)$_2$, $SO_2$(alkyl), SO(alkyl), SO(aryl), $SO_2$(aryl), $SO_3$(alkyl), $SO_3$(aryl), S-alkyl, S-aryl, NH—CO(alkyl), $CO_2$(alkyl), $CONH_2$, CO(alkyl), NHCOH, $NHCO_2$(alkyl), CO(aryl), $CO_2$(aryl) radical, wherein two or more adjacent radicals, each independently of the other(s), may also be linked to one another so that a condensed ring system is present and wherein in $R^2$ to $R^9$ alkyl represents a hydrocarbon radical having from 1 to 20 carbon atoms which may in each case be linear or branched, alkenyl represents a mono- or poly-unsaturated hydrocarbon radical having from 2 to 20 carbon atoms which may in each case be linear or branched, and cycloalkyl represents a hydrocarbon having from 3 to 20 carbon atoms, wherein the alkyl, alkenyl and cycloalkyl groups may also carry further substituents as defined for $R^1$. Preferred substituents in this connection are selected from the group Br, Cl, F, ($C_1$-$C_{12}$)-alkyl, O—($C_1$-$C_{12}$)-alkyl, phenyl, O-phenyl, NH(($C_1$-$C_{12}$)-alkyl), N(($C_1$-$C_{12}$)-alkyl)$_2$, and aryl represents a 5- to 14-membered aromatic radical in which from one to four carbon atoms may also be replaced by hetero atoms from the group nitrogen, oxygen and sulfur so that a 5- to 14-membered heteroaromatic radical is present and wherein the aryl or heteroaryl radical may carry further substituents as defined for $R^1$, preferred substituents being selected from the group Br, Cl, F, ($C_1$-$C_{12}$)-alkyl, O—($C_1$-$C_{12}$) -alkyl, phenyl, O-phenyl, $NH_2$, NH(($C_1$-$C_{12}$)-alkyl), N(($C_1$-$C_{12}$)-alkyl)$_2$.

The mentioned alkyl radicals have preferably from 1 to 10 carbon atoms, particularly preferably from 1 to 5. The alkenyl radicals have preferably from 2 to 10 carbon atoms, particularly preferably from 2 to 5. The cycloalkyl radicals have preferably from 3 to 8 carbon atoms. The aryl radicals have preferably from 6 to 10 carbon atoms, the heteroaryl radicals from 4 to 9.

Preference is given to ligands wherein X is $CR^2$ and Y is $CR^9$, yielding compounds of formula (II)

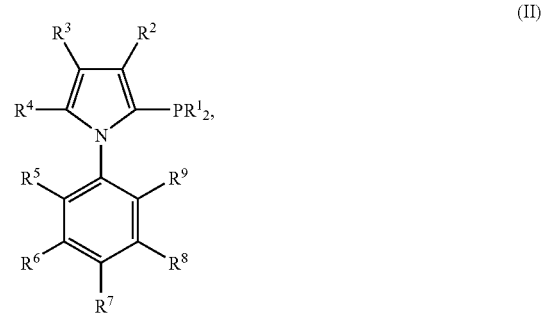

wherein the radicals $R^1$ to $R^9$ are as defined above. In a further preferred embodiment, X is nitrogen and Y is a $CR^9$ group.

Preferred ligands of formula (I) or (II) carry at least one radical $R^1$ selected from the group consisting of phenyl, $C_1$-$C_{10}$-alkyl, cyclopentyl, cyclohexyl, cycloheptyl, 1-adamantyl, 2-adamantyl, 5H-dibenzophospholyl, 9-phospha-bicyclo[3.3.1]nonanyl, 9-phosphabicyclo[4.2.1]nonanyl radicals. Examples of preferred $C_1$-$C_{10}$-alkyl- radicals are methyl, ethyl, n-propyl, 1-methylethyl, n-butyl, 1-methylpropyl, 1,1-dimethylethyl, n-pentyl, 1-methylbutyl, 2-methylbutyl, 3-methylbutyl, 2,2-dimethylpropyl, 1-ethyl-propyl, n-hexyl, 1,1-dimethylpropyl, 1,2-dimethylpropyl, 1-methylpentyl, 2-methylpentyl, 3-methylpentyl, 4-methyl-pentyl, 1,1-dimethylbutyl, 1,2-dimethylbutyl, 1,3-dimethyl-butyl, 2,2-dimethylbutyl, 2,3-dimethylbutyl, 3,3-dimethyl-butyl, 1-ethylbutyl, 2-ethylbutyl, 1,1,2-trimethylpropyl, 1,2,2-trimethylpropyl, 1-ethyl-1-methylpropyl, n-heptyl, n-octyl, n-nonyl, n-decyl, particular preference being given especially to the isopropyl radical and the tert-butyl radical.

Preferred radicals $R^2$ to $R^9$ are selected from the group hydrogen, $C_1$-$C_{10}$-alkyl, $C_2$-$C_{10}$-alkenyl, $C_1$-$C_{10}$-haloalkyl, $C_3$-$C_8$-cycloalkyl, $C_6$-$C_{10}$-aryl, which includes especially also phenyl, naphthyl, fluorenyl, and $C_2$-$C_6$-heteroaryl, wherein from 1 to 3 nitrogen atoms or an oxygen or sulfur atom may be present as hetero atom, and wherein two adjacent radicals $R^2$ to $R^9$ may be bridged with one another, there preferably being formed a 4- to 8-membered, preferably aromatic ring.

The ligands according to the invention can be prepared by reacting the corresponding phenylpyrrole derivative in the presence of a strong base, such as, for example, an alkyllithium compound, and subsequently adding a halophosphane, in accordance with the following reaction scheme, which is given by way of example

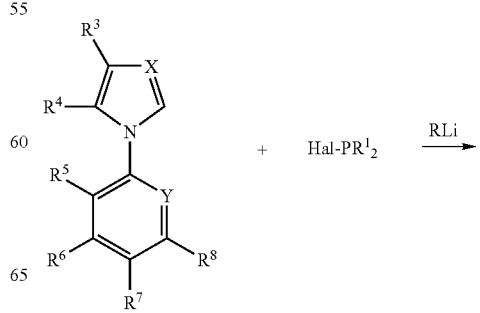

-continued

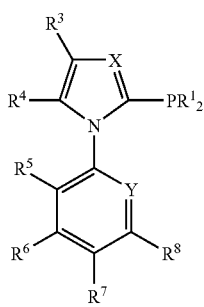

According to the invention, the novel phosphane ligands are used as catalysts in combination with transition metal complexes or transition metal salts of sub-group VIII of the periodic system of the elements, such as, for example, palladium, nickel, platinum, rhodium, iridium, ruthenium, cobalt. The ligands according to the invention can generally be added in situ to corresponding transition metal precursor compounds and accordingly used for catalytic applications. However, it may occasionally be advantageous for specific mono-, di-, tri- or tetra-phosphane complexes of the mentioned transition metals to be prepared first and subsequently used for catalysis reactions. The catalytic activity can thereby be increased further in some catalyst systems.

As transition metal compounds there are preferably used palladium or nickel compounds and particularly preferably palladium compounds.

The ligands according to the invention are generally added in situ preferably to nickel(II) or palladium(II) salts or to nickel(II), palladium(II) or nickel(0) or palladium(0) complexes. Preferred palladium complexes are, for example, palladium(II) acetate, palladium(II) chloride, palladium(II) bromide, lithium tetrachloropalladate(II), palladium(II) acetylacetonate, palladium(0) -dibenzylidene-acetone complexes, palladium(0) tetrakis(triphenyl-phosphane), palladium(0) bis(tri-o-tolylphosphane), palladium(II) propionate, palladium (II) bis(triphenyl-phosphane) dichloride, palladium(0) diallyl ether complexes, palladium(II) nitrate, palladium(II) chloride bis(acetonitrile), palladium(II) chloride bis (benzo-nitrile).

In catalytic applications, the phosphane ligand is generally used in excess relative to the transition metal. The ratio of transition metal to ligand is preferably from 1:1 to 1;1000. Ratios of transition metal to ligand of from 1:1 to 1:100 are particularly preferred. The exact transition metal/ligand ratio to be used depends on the concrete application, but also on the amount of catalyst used. Accordingly, it is generally customary to use low transition metal/ligand ratios at very low transition metal concentrations (<0.01 mol. %) than at transition metal concentrations of from 0.5 to 0.01 mol. % transition metal.

The catalysts are preferably used at temperatures of from 20 to 200° C.; in many cases, it has proved advantageous to work at temperatures of from 30 to 180° C., preferably from 40 to 160° C. The ligands can also be used without any loss of activity in reactions under pressure, reactions usually being carried out only up to a pressure of 100 bar, but preferably in the range of from normal pressure to 60 bar.

When carrying out catalytic reactions using ligands of formula (I), high turnover rates (TON) can be achieved with a low catalyst concentration. The transition metal is preferably used in a ratio of from 5 mol. % to 0.001 mol. %, particularly preferably from 0.5 mol. % to 0.01 mol. %, relative to the substrate.

The phosphane ligands prepared in accordance with the invention have proved suitable especially as the ligand component for the catalytic preparation of arylated olefins (Heck reactions), biaryls (Suzuki reactions), α-aryl ketones and amines from aryl halides or vinyl halides. However, it is obvious to the person skilled in the art that the novel catalyst systems can also be used to catalyse other transition-metal-catalysed reactions, such as metathesis or hydrogenations of double bonds or carbonyl compounds, but especially palladium- and nickel-catalysed carbonylations of aryl halides, alkynylations using alkynes (Sonogashira couplings), cross-couplings using organometallic reagents, such as, for example, zinc reagents or tin reagents.

A particular advantage of the ligands according to the invention is the high degree of activity induced by the ligands in the activation of readily available but inert chloroaromatic compounds. The described catalyst and ligand systems can accordingly be used for large-scale purposes.

The phosphanes prepared in accordance with the invention can be used in the preparation of aryl olefins, dienes, diaryls, benzoic acid derivatives, acrylic acid derivatives, arylalkanes, alkynes, amines. The compounds so prepared are used, for example, as UV absorbers, as intermediates for pharmaceuticals and agrochemicals, as ligand precursors for metal-locene catalysts, as perfumes, as active ingredients having biological activity and as structural units for polymers.

IMPLEMENTATION EXAMPLES

General

Reactions of compounds sensitive to air were carried out in an argon-filled glove-box or in standard Schlenk tubes. The solvents tetrahydrofuran (THF), diethyl ether and dichloromethane were degassed and rendered absolute by means of a solvent-drying installation (Innovative Technologies) by filtration through a column packed with activated aluminium oxide. Toluene and pentane were additionally freed of oxygen using a column packed with a copper catalyst.

The Examples which follow serve to explain the invention without limiting it thereto.

Preparation of Ligands 1 to 3 (L1 to L3):

10 mmol. of phenylpyrrole are dissolved under argon in 20 ml of absolute hexane. 10 mmol. of TMEDA and 10 mmol. of n-BuLi (1.6 M in hexane) are added at room temperature. After three hours' heating under reflux, a yellow suspension is obtained. It is cooled to room temperature, and 10 mmol. of C1-PR$^1_2$ are slowly added thereto. After reacting for one hour under reflux, hydrolysis is carried out at room temperature using 15 ml of degassed water. The organic phase is transferred to a separating funnel, under argon, with the aid of a cannula. The aqueous phase is extracted twice using 15 ml of hexane each time. The hexane fractions are likewise transferred to the separating funnel. The combined organic phases are washed with 15 ml of degassed water and dried over degassed sodium sulfate. The solvents are distilled off and the viscous residue is dissolved in methanol with heating. After one day at room temperature, the mixture is cooled for four hours at 0° C. The resulting white solid is filtered off and dried in vacuo (purity 90-95%).

Yields:

$PR^1_2$=$PCy_2$ 72% ($^{31}$P—NMR: −28.0 ppm) (L1; N—PHOS-Cy):

$PR^1_2$=$PPh_2$ 64% ($^{31}$P—NMR: −29.8 ppm) (L2; N—PHOS-Ph)

$PR^1_2$=$P^tBu_2$ 40% ($^{31}$P—NMR: 3.6 ppm) (L3; N—PHOS-$^t$Bu)

CATALYSIS EXAMPLES 1 to 32

Suzuki Couplings 1.25 mmol. of phenylboronic acid and 2.00 mmol. of base are weighed into 2.5 ml glass bottles. These bottles are purged with argon and sealed. All further stock solutions are prepared under argon.

Solution S-1: 147 mmol. of 2-chlorotoluene, 58 mmol. of tetradecane, 155 ml of abs. toluene Solution S-2: 150 mmol. of 4-chloroanisole, 57 mmol. of tetradecane, 154 ml of abs. toluene Solution M-1: 0.073 mmol.$_{pd}$ of palladium(II) acetate, 49 ml of abs. toluene Solution M-2: 0.065 mmol.$_{pd}$ of tris-(dibenzylideneacetone)-dipalladium(0), 49 ml of abs. toluene Solution L-1: 0.04 mmol. of N—PHOS-Cy (L1), 10 abs. toluene Solution L-2: 0.08 mmol. of N—PHOS-tBu (L3), 21 abs. toluene The following solutions are mixed under Ar and stirred for about 1 hour at room temperature (reaction metal precursor with ligand):

|  | Ligand | Metal precursor |
|---|---|---|
| M-L-1 | 5.0 ml L-1 | 7.5 ml M-1 |
| M-L-2 | 5.0 ml L-1 | 7.5 ml M-2 |
| M-L-3 | 10.5 ml L-2 | 16.0 ml M-1 |
| M-L-4 | 10.5 ml L-2 | 16.0 ml M-2 |

A Vantage synthesizer is used to pipette the following amounts of the resulting solutions into the Vantage vials:

1. 1.25 ml of S-1 (No. 1-8), (No. 17-24) 1.25 ml of S-2 (No. 9-16), (No. 25-32)
2. 1.25 ml of M-L-1 (No. 1-16) or 1.25 ml of M-L-2 (No. 17-32).

Using the Vantage mixing/heating unit, the Vantage vials so filled are heated for 4.0 hours at 110° C. (Vantage setting) with shaking (1000 rpm) (heating phase 0.5 h/internal temperature about 120° C.).

After the reaction, 1.0 ml of each reaction solution is filtered over silica gel. The solution so obtained is analysed by means of GC. The yields of the individual conversions are summarised in Table 1.

TABLE 1

Summary of the results of Catalysis Examples 1 to 32

| No. | Starting material [mmol.] | Lig. | Metal precursor Name | mol. %$_{pd}$ | Ligand eq. to Pd | Base Name | Eq. to starting material | Yield (%) |
|---|---|---|---|---|---|---|---|---|
| 1 | 1.0 | L-1 | Pd(OAc)$_2$ | 0.1 | 2 | K$_3$PO$_4$ | 2 | 83.8/89.1 |
| 2 | 1.0 | L-1 | Pd(OAc)$_2$ | 0.1 | 2 | K$_2$CO$_3$ | 2 | 78.4/85.0 |
| 3 | 1.0 | L-1 | Pd(OAc)$_2$ | 0.1 | 2 | NaOAc | 2 | 9.1/7.8 |
| 4 | 1.0 | L-1 | Pd(OAc)$_2$ | 0.1 | 2 | Cs$_2$CO$_3$ | 2 | 51.0/60.8 |
| 5 | 1.0 | L-1 | Pd$_2$(dba)$_3$ | 0.1 | 2 | K$_3$PO$_4$ | 2 | 94.0/89.8 |
| 6 | 1.0 | L-1 | Pd$_2$(dba)$_3$ | 0.1 | 2 | K$_2$CO$_3$ | 2 | 94.8/93.0 |
| 7 | 1.0 | L-1 | Pd$_2$(dba)$_3$ | 0.1 | 2 | NaOAc | 2 | 34.4/35.2 |
| 8 | 1.0 | L-1 | Pd$_2$(dba)$_3$ | 0.1 | 2 | Cs$_2$CO$_3$ | 2 | 57.7/53.7 |
| 9 | 1.0 | L-1 | Pd(OAc)$_2$ | 0.1 | 2 | K$_3$PO$_4$ | 2 | 60.3/64.8 |
| 10 | 1.0 | L-1 | Pd(OAc)$_2$ | 0.1 | 2 | K$_2$CO$_3$ | 2 | 28.0/40.5 |
| 11 | 1.0 | L-1 | Pd(OAc)$_2$ | 0.1 | 2 | NaOAc | 2 | 3.6/3.7 |
| 12 | 1.0 | L-1 | Pd(OAc)$_2$ | 0.1 | 2 | Cs$_2$CO$_3$ | 2 | 36.3/10.0 |
| 13 | 1.0 | L-1 | Pd$_2$(dba)$_3$ | 0.1 | 2 | K$_3$PO$_4$ | 2 | 84.8/95.8 |
| 14 | 1.0 | L-1 | Pd$_2$(dba)$_3$ | 0.1 | 2 | K$_2$CO$_3$ | 2 | 65.5/68.2 |
| 15 | 1.0 | L-1 | Pd$_2$(dba)$_3$ | 0.1 | 2 | NaOAc | 2 | 23.5/24.0 |
| 16 | 1.0 | L-1 | Pd$_2$(dba)$_3$ | 0.1 | 2 | Cs$_2$CO$_3$ | 2 | 34.7/27.2 |
| 17 | 1.0 | L-2 | Pd(OAc)$_2$ | 0.1 | 2 | K$_3$PO$_4$ | 2 | 61.4/84.5 |
| 18 | 1.0 | L-2 | Pd(OAc)$_2$ | 0.1 | 2 | K$_2$CO$_3$ | 2 | 52.5/50.1 |
| 19 | 1.0 | L-2 | Pd(OAc)$_2$ | 0.1 | 2 | NaOAc | 2 | 19.4/16.5 |
| 20 | 1.0 | L-2 | Pd(OAc)$_2$ | 0.1 | 2 | Cs$_2$CO$_3$ | 2 | 18.1/12.8 |
| 21 | 1.0 | L-2 | Pd$_2$(dba)$_3$ | 0.1 | 2 | K$_3$PO$_4$ | 2 | 98.9/96.1 |
| 22 | 1.0 | L-2 | Pd$_2$(dba)$_3$ | 0.1 | 2 | K$_2$CO$_3$ | 2 | 93.4/91.3 |
| 23 | 1.0 | L-2 | Pd$_2$(dba)$_3$ | 0.1 | 2 | NaOAc | 2 | 17.4/6.1 |
| 24 | 1.0 | L-2 | Pd$_2$(dba)$_3$ | 0.1 | 2 | Cs$_2$CO$_3$ | 2 | 36.5/31.7 |
| 25 | 1.0 | L-2 | Pd(OAc)$_2$ | 0.1 | 2 | K$_3$PO$_4$ | 2 | 83.5/97.3 |
| 26 | 1.0 | L-2 | Pd(OAc)$_2$ | 0.1 | 2 | K$_2$CO$_3$ | 2 | 74.1/60.1 |
| 27 | 1.0 | L-2 | Pd(OAc)$_2$ | 0.1 | 2 | NaOAc | 2 | 33.2/39.4 |
| 28 | 1.0 | L-2 | Pd(OAc)$_2$ | 0.1 | 2 | Cs$_2$CO$_3$ | 2 | 69.6/66.4 |
| 29 | 1.0 | L-2 | Pd$_2$(dba)$_3$ | 0.1 | 2 | K$_3$PO$_4$ | 2 | 91.5/99.6 |
| 30 | 1.0 | L-2 | Pd$_2$(dba)$_3$ | 0.1 | 2 | K$_2$CO$_3$ | 2 | 81.7 |
| 31 | 1.0 | L-2 | Pd$_2$(dba)$_3$ | 0.1 | 2 | NaOAc | 2 | 26.6/24.5 |
| 32 | 1.0 | L-2 | Pd$_2$(dba)$_3$ | 0.1 | 2 | Cs$_2$CO$_3$ | 2 | 71.5/56.7 |

CATALYSIS EXAMPLES 33 to 59

Suzuki Reaction of Aryl Chlorides with Phenylboronic Acid/-pyrrolylphosphanes $$R-Ar-Cl + PhB(OH)_2 \rightarrow R-Ar-Ph$$

Reagents: 3 nmol. of ArCl, 4.5 mmol. of $PhB(OH)_2$, 6 mmol. of $K_3PO_4$, $Pd(OAc)_2$, Pd/L=1:2, 6 ml of toluene, 20 hours. The reaction is carried out as a one-pot reaction under protecting gas. Working-up is carried out with 10 ml of each of methylene chloride and 1N sodium hydroxide solution. The reaction is monitored by means of GC, internal GC standard: hexadecane.

The starting materials used and the results of the conversions are summarised in Table 2.

TABLE 2

Summary of the results of Catalysis Examples 33 to 59

| No. | R | Ligand | Conc. [mol. %] | T [° C.] | C [%] | Yield (averaged) [%] | TON |
|---|---|---|---|---|---|---|---|
| Aromatic compounds |||||||| 
| 33 | 4-$CF_3$ | $PtBu_2$ | 0.01 | 60 | 71-84 | 74 | 7400 |
| 34 | 4-COMe | $PtBu_2$ | 0.01 | 60 | 100 | 100 | 10,000 |
| 35 | 4-CN | $PtBu_2$ | 0.01 | 60 | 100 | 100 | 10,000 |
| 36 | H | $PtBu_2$ | 0.01 | 60 | 83-98 | 96 | 9600 |
| 37 | 4-Me | $PtBu_2$ | 0.01 | 60 | 98-100 | 99 | 9900 |
| 38 | 4-Ome | $PtBu_2$ | 0.01 | 60 | 73-89 | 80 | 8000 |
| 39 | 2-$CF_3$ | $PtBu_2$ | 0.05 | 60 | 91 | | |
| 40 | 2-$CF_3$ | $PCy_2$ | 0.05 | 60 | 99 | 95 | |
| 41 | 2-$CF_3$ | $PAd_2$ | 0.05 | 60 | 75 | | |
| 42 | 2-COMe | $PtBu_2$ | 0.05 | 60 | 78-84 | 85 | |
| 43 | 2-COMe | $PCy_2$ | 0.05 | 60 | 55 | | |
| 44 | 2-COMe | $PAd_2$ | 0.05 | 60 | 70 | | |
| 45 | 2-CN | $PtBu_2$ | 0.05 | 60 | 100 | 100 | 2000 |
| 46 | 2-CN | $PCy_2$ | 0.05 | 60 | 100 | 100 | 2000 |
| 47 | 2-CN | $PAd_2$ | 0.05 | 60 | 100 | 99 | 1980 |
| 48 | 2-Me | $PtBu_2$ | 0.01 | 60 | 80-87 | 81 | 8100 |
| 49 | 2-Ome | $PtBu_2$ | 0.01 | 60 | 97-100 | 97 | 9700 |
| 50 | 2-F | $PtBu_2$ | 0.01 | 60 | 100 | 97 | 9700 |
| 51 | 2,6-$Me_2$ | $PtBu_2$ | 0.05 | 60 | 20-22 | 16 | 320 |
| 52 | 2,6-$Me_2$ | $PCy_2$ | 0.05 | 60 | 76 | 72 | 1440 |
| 53 | 2,6-$Me_2$ | $PAd_2$ | 0.05 | 60 | 18 | 15 | 300 |
| Heterocycles ||||||||
| 54 | 3-chloro-pyridine | $PtBu_2$ | 0.01 | 60 | 99-100 | 99 | 9900 |
| 55 | 2-chloro-quinoline | $PtBu_2$ | 0.05 | 60 | 100 | 87 | 1740 |
| 56 | 5-chloro-indole | $PtBu_2$ | 0.05 | 100 | 97-100 | 90 | |
| 57 | 2-chloro-benzoxazole | $PtBu_2$ | 0.05 | 100 | 99 | 0[a] | 0 |
| 58 | 3-chloro-thiophene | $PtBu_2$ | 0.05 | 100 | 11 | 5 | 100 |
| 59 | 5-chloro-furfural | $PtBu_2$ | 0.05 | 100 | 100 | 99 | 1980 |

[a] unknown (not visible in the GC) decomposition products. Both starting material and product withstand the basic working-up undamaged. Decomposition (>60%) but scarcely any product (<10%) is observed even at a reaction temperature of 60° C.

EXAMPLES 60 to 64

Examples of Ligand Syntheses

EXAMPLE 60

Synthesis of N-phenyl-2-(di-1-adamantyl-phosphino)pyrrole

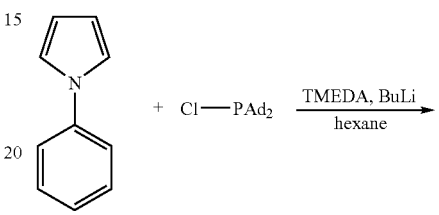

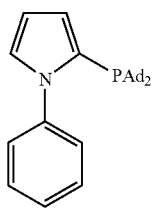

1.6 ml of TMEDA (15 mmol.) are added to a suspension of 1.43 g (10 mmol.) of N-phenylpyrrole in 30 ml of hexane. 6.25 ml of 1.6 molar n-butyllithium solution (10 mmol.) are added at room temperature. The mixture is then heated for 2.5 hours at reflux temperature (solution 1). In another flask, 3.36 g (10 mmol.) of di-1-adamantylchlorophosphane are mixed with 40 ml of hexane and heated to 76° C. (solution 2). The boiling solution 1 is then slowly transferred into solution 2, which is at 76° C., by means of a cannula. The mixture is then boiled for a further 2 hours at reflux, the solution is cooled, and 20 ml of water are added thereto. The organic phase is filtered off over magnesium sulfate. The solution is concentrated in vacuo; 15 ml of toluene are added thereto, and the mixture is heated to 60° C. and then cooled. After one day at room temperature, the product is filtered off. Yield: 3.3 g (75%).

$^{31}$P NMR (161 MHz, $CDCl_3$): δ=−4.5.

$^1$H NMR (400 MHz, $CDCl_3$): δ=1.7 (bs, 16H), 1.7-2.0 (m, 22H), 6.4 (dd, $J_1$=8.6, 12.8, $J_2$=3.5, 1H), 6.75 (dd, $J_1$=3.5, $J_2$=1, 1H), 6.9-7.0 (m, 1H), 7.25-7.3 (m, 2H), 7.35-7.45 (m, 3H).

$^{13}$C NMR (100.6 MHz, $CDCl_3$): δ=28.6 (d, $J_{PC}$=11.5), 37, 37.5 (d, $J_{PC}$=17.2), 41.6 (d, $J_{PC}$=11.5), 108.2, 119.5 (d, $J_{PC}$=4.7), 125.8, 126 (d, $J_{PC}$=10.8), 127.3, 128.2, 128.3 (d, $J_{PC}$=3.8), 141.6 (d, $J_{PC}$=1.9).

MS: m/z (%): 443 (68), 308 (13), 172 (14), 135 (100), 107 (7), 93 (19), 79 (17).

HRMS: $C_{30}H_{38}NP$: calc. 443.2742; found 443.26775.

EXAMPLE 61

Synthesis of 1-mesityl-2-(dicyclohexyl-phosphino)imidazole

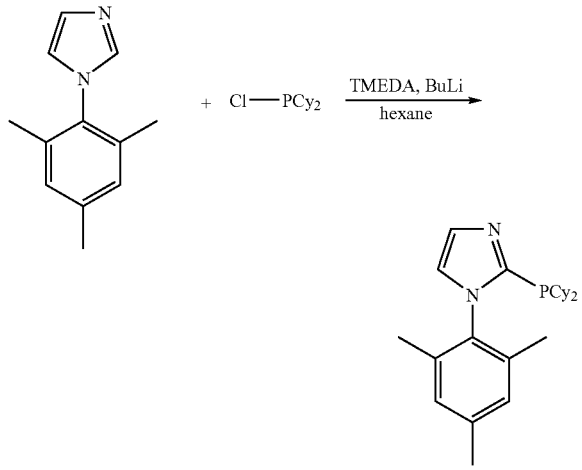

1.6 ml of TMEDA (15 mmol.) are added to a suspension of 1.86 g (10 mmol.) of N-mesitylimidazole in 30 ml of hexane. 6.25 ml of 1.6 molar n-butyllithium solution (10 mmol.) are added at room temperature. The mixture is then heated for 2.5 hours at reflux temperature (solution 1). In another flask, 2.2 ml (10 mmol.) of dicyclohexylchlorophosphane are mixed with 20 ml of hexane and heated to 60° C. (solution 2). The boiling solution 1 is then slowly transferred into solution 2, which is at 60° C., by means of a cannula. The mixture is then boiled for a further 1 hour at reflux, the solution is cooled, and 20 ml of degassed water are added thereto. The organic phase is filtered off over magnesium sulfate. The solution is concentrated in vacua; 30 ml of pentane are added thereto, and the mixture is boiled for 1 hour at reflux. The product precipitates in crystalline form at −30° C. and is filtered off while cold. Yield: 2.48 g (65%)

$^{31}$P NMR (161 MHz, CDCl$_3$): δ=−18.9.

$^{1}$H NMR (400 MHz, CDCl$_3$): δ=0.9-1.2 (m, 11H), 1.5-1.7 (m, 11H), 1.9 (s, 6H), 1.9-2.0 (m, 2H), 2.2 (s, 3H), 6.8-6.9 (m, 3H), 7.3 (S, 1H).

13C NMR (100.6 MHz, CDCl$_3$): δ=18.5, 20.9, 26.9, 27.5, 27.7 (d, J=9.5), 30.4 (d, J=14.3), 30.9 (d, J=10.5), 34.6 (d, J=9.5), 122.7, 129.2, 131.5, 134.9, 135.5, 138.2, 147.5 (d, J=16.2).

MS; m/z (%): 382 (11), 299 (100), 217 (24), 202 (7), 185 (27), 83 (7), 55 (21).

EXAMPLE 62

Synthesis of N-(2-methoxyphenyl)-2-(dicyclo-hexylphosphino)pyrrole a) Synthesis of N-(2-methoxyphenyl)pyrrole

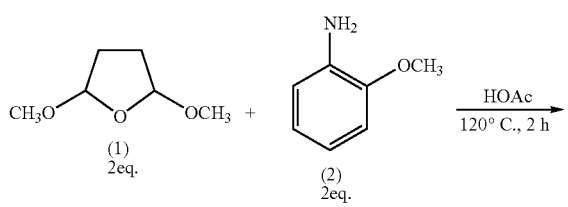

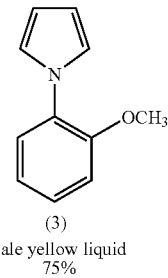

(3)
pale yellow liquid
75%

Lit.: Faigl, F.; Fogassy, K.; Thuner, A.; Toke, L.; *Tetrahedron* 1997, 53, 4883.

10.95 g (83 mmol.) of 1 and 4.7 g (38 mmol.) of 2 are refluxed for 2 hours in 10 ml of glacial acetic acid. The colour of the solution changes from yellow through red to black. The mixture is then diluted with 75 ml of distilled water and extracted twice with 100 ml of CH$_2$Cl$_2$. Na$_2$CO$_3$ is added to the black organic solutions. After filtration and concentration (20 mbar, 50° C.), a black oil is obtained and is distilled in vacuo. Yield: 4.45 g (25.7 mmol.; 75%).

$^{1}$H NMR (25° C., CDCl$_3$): δ (ppm)=3.8 (s, 3H), 6.3 (t, J=2.2 Hz, 2H), 7.0 (m, 4H), 7.3 (m, 2H).

b) Synthesis of N-(2-methoxyphenyl)-2-(dicyclohexyl-phosphino)pyrrole

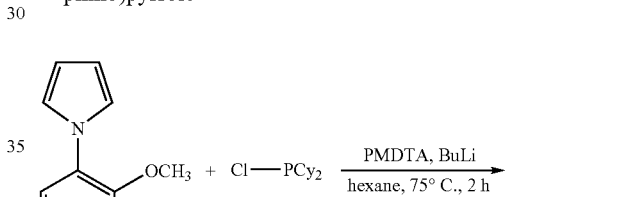

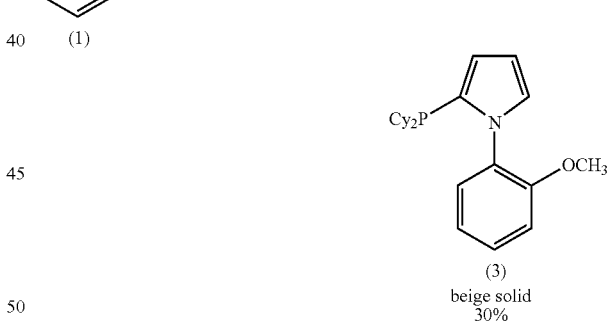

(3)
beige solid
30%

3.14 ml (15 mmol.) of N,N,N',N',N''-pentamethyldiethylene-triamine (PMDTA) are added to a solution of 1.73 g (10 mmol.) of 1 in 30 ml of hexane. A solution (1.6 M in hexane) of n-BuLi (6.25 ml, 10 mmol.) is added dropwise. After 3 hours under reflux (75° C.), the colour of the solution has changed from yellow to black. Without cooling this mixture, 2.2 ml (10 mmol.) of chlorodicyclohexyl-phosphane dissolved in 20 ml of hexane are added dropwise. Refluxing is carried out for a further one hour. The colour of the solution lightens to orange, and a white precipitate forms. After cooling to room temperature, 30 ml of water are added to the mixture. The orange organic phase is extracted 3 times using 20 ml of hexane each time. The combined organic phases are washed with 10 ml of water and filtered over Na$_2$SO$_4$. The solvent is removed in vacuo (45° C.). The viscous orange residue is refluxed for 30 minutes in 30 ml of MeOH. On cooling to RT, the product precipitates and is filtered off (1.1 g, 30%).

$^1$H NMR (25° C., C$_6$D$_6$): δ (ppm)=1.1-1.9 (m, 22H), 3.2 (s, 3H), 7.0 (m, 4H), 6.5-7.2 (m, 3H).

$^{13}$C NMR (25° C., C$_6$D$_6$): δ (ppm)=27.2, 27.7, 27.8, 29.6, 30.9, 34.9, 55.1, 109.8, 111.8, 116.5, 116.6, 120.2, 123.6, 129.3, 130.9, 136.3, 156.0.

$^{31}$P NMR (25° C., C$_6$D$_6$): δ (ppm) −26.8.

EXAMPLE 63

Synthesis of N-phenyl-2-(dicyclohexyl-phosphino)indole a) Synthesis of N-phenylindole

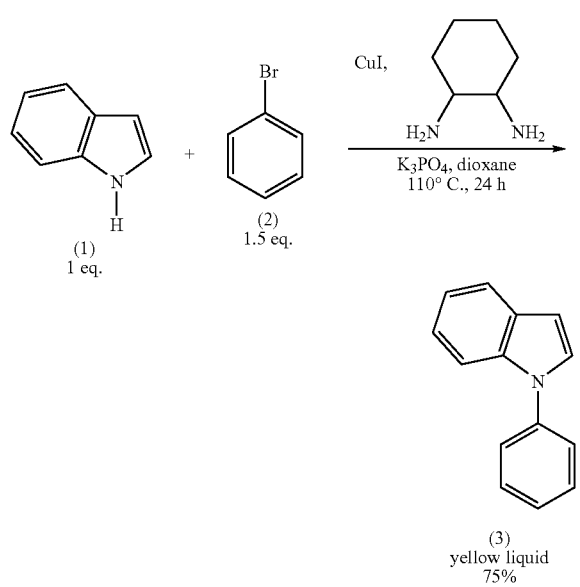

Lit.: Synthesis: Klapars, A.; Antilla, J.; Huang, X.; Buchwald, S. *J. Am. Chem. Soc.* 2001, 123, 7721. Analysis: (a) Nishio, T. *J. Org. Chem.* 1988, 53, 1323. (b) Belier, M.; Breindl, C.; Riermeier, T.; Tillack, A. *J. Org. Chem.* 2001, 66, 1403.

0.19 g (0.1 nmol.) of CuI, 2.34 g (20 mmol.) of 1, 8.82 g (42 mmol.) of K$_3$PO$_4$, 0.48 ml (4 mmol.) of 1,2-diaminocyclohexane and 3.16 ml (30 mmol.) of 2 are stirred for 24 hours at 110° C. in 20 ml of dry dioxane. The mixture is then diluted with 50 ml of ethyl acetate. The violet precipitate is filtered off over silica gel, yielding a yellow solution, which is concentrated in vacuo (20 mbar, 50° C.). The orange oil that remains is purified by column chromatography (silica gel, hexane/ethyl acetate 98/2). Yield: 3.0 g (15.5 mmol.; 75%).

$^1$H NMR (25° C., CDCl$_3$): δ (ppm)=6.45 (m, 1H), 6.9-7.5 (m, 10H).

$^{13}$C NMR (25° C., CDCl$_3$): δ (ppm)=104.1, 111.1, 120.9, 121.7, 122.9, 124.9, 126.9, 128.5, 129.9, 130.1, 130.6, 132.1, 136.4, 140.3.

b) Synthesis of N-phenyl-2-(dicyclohexylphosphino)indole

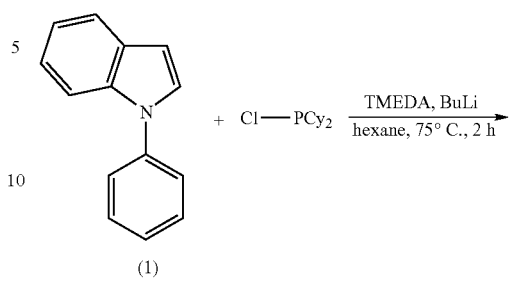

1.6 ml (15 mmol.) of TMEDA are added to 1.93 g (10 mmol.) of 1 in 30 ml of hexane. A solution (1.6 M in hexane) of n-BuLi (6.25 ml, 10 mmol.) is added dropwise. After 3 hours, reflux (75° C.), the colour has deepened from yellow to orange. Without cooling, a solution of 2.2 ml (10 mmol.) of chlorodicyclohexylphosphane in 20 ml of hexane is added dropwise. Refluxing is carried out for a further one hour, the colour of the mixture lightening again and a white solid precipitating. After cooling, 30 ml of water are added to the mixture. The aqueous phase is extracted 3 times using 20 ml of hexane each time. The combined organic phases are washed with 10 ml of water, dried over Na$_2$SO$_4$ and concentrated in vacuo (45° C.). The yellow residue is boiled for 30 minutes in 30 ml of MeOH. After cooling to RT, the resulting product is filtered off (660 mg, 17%).

$^{31}$P NMR (25° C., C$_6$D$_6$): δ (ppm)=−24.8.

EXAMPLE 64

Synthesis of N-(naphthyl)-2-(dicyclohexyl-phosphino)pyrrole a) Synthesis of N-naphthylpyrrole

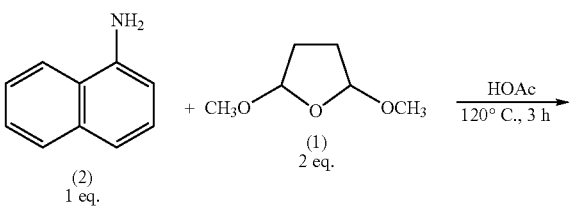

-continued

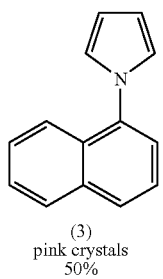

(3)
pink crystals
50%

Lit.: Analysis: (a) Paredes, E.; Biolatto, B.; Kneeteman, M.; Mancini, P. *Tetrahedron Lett.* 2000, 41, 8079. (b) Gross, H. *Chem. Ber.* 1962, 95, 2270.

10.95 g (83 mmol.) of 1 are added to a violet solution of 5.44 g (38 mmol.) of 2 in 10 ml of glacial acetic acid. The resulting brown solution is refluxed for 3 hours under argon (120° C.), whereupon its colour changes to black. The solution is concentrated to half the volume in vacuo (20 mbar, 50° C.) before being hydrolysed with 20 ml of water. The organic phase is extracted with $CH_2Cl_2$ (3×30 ml), dried over $Na_2SO_4$ and concentrated (20 mbar, 50° C.), there being obtained a black oil which is purified by column chromatography (silica gel, hexane/ethyl acetate 85/15). Yield: 3.53 g (18.3 mmol.) of a red oil which, crystallises at −25° C. (pink crystals).

$^1$H NMR (25° C., CDCl$_3$): δ (ppm)=6.3 (t, J=2.2 Hz, 2H), 6.7 (t, J=2.2 Hz, 2H), 6.9-7.2 (m, 4H), 7.3 (d, 8.1 Hz, 1H), 7.4 (d, 8.1 Hz, 1H), 7.7 (d, 8.1 Hz, 1H).

$^{13}$C NMR (25° C., CDCl$_3$): δ (ppm)=110.0, 123.6, 123.8, 123.9, 125.7, 126.9, 127.4, 128.2, 130.7, 134.9, 139.0.

Elemental analysis: found (%) C 86.7 (th: 87.0), H 5.89 (5.70), N 7.29 (7.30).

b) Synthesis of N-(naphthyl)-2-(dicyclohexylphosphino)-pyrrole

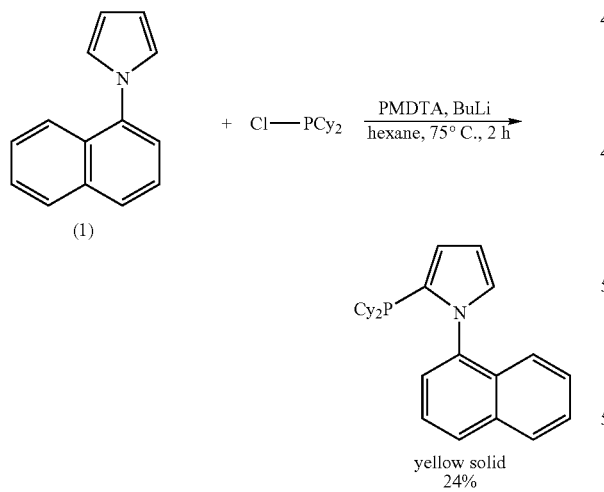

yellow solid
24%

1.6 ml (15 mmol.) of TMEDA are added to a solution of 1.93 g (10 mmol.) of 1 in 30 ml of hexane. A solution (1.6 M in hexane) of n-BuLi (6.25 ml, 10 mmol.) is added dropwise. After 3 hours reflux (75° C.), the colour has changed from orange through green to black. Without cooling, a solution of 2.2 ml (10 mmol.) of chlorodicyclo-hexylphosphane in 20 ml of hexane is added dropwise and refluxing is carried out for a further one hour. The colour of the solution changes to yellow, and a white precipitate forms. After cooling to RT, 30 ml of water are added to the mixture. The aqueous phase is extracted 3 times using 20 ml of hexane each time. The combined organic phases are washed with 10 ml of water, dried over $Na_2SO_4$ and concentrated in vacuo (45° C.). The orange oil that remains is refluxed for 30 minutes in 30 ml of MeOH (60° C.). On cooling to −25° C., the product precipitates in the form of a yellow solid and is filtered off (0.9 g, 24%).

$^{31}$P NMR (25° C., C$_6$D$_6$): δ (ppm)=−23.3.

EXAMPLE 65

Ligands:

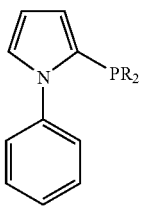 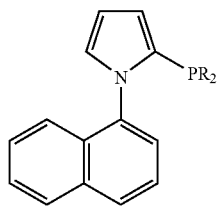

1 R = Ph (yield = 75%)
2 R = Cy (80)
3 R = tBu (75)
4 R = Ad (85)

5 R = Cy (15)
6 R = tBu (15)

N-arylpyrrole based ligand.

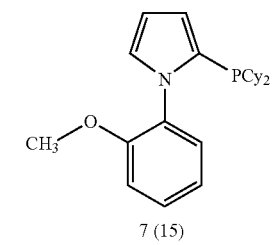

7 (15)

8 R = Cy (60)
9 R = tBu (50)
10 R = Ad (45)

N-arylindole based ligand.

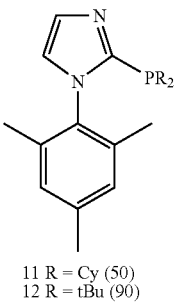 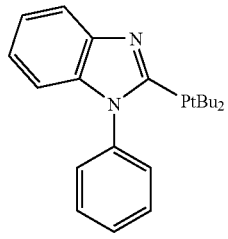

11 R = Cy (50)
12 R = tBu (90)

13 (10)

N-arylimidazole based ligand.

General Procedure:

In a three nacked 100 ml round bottom flask with reflux condenser, N-arylpyrrole (or N-arylindole or N-arylimidazole) (10 mmol) was dissolved in 20 ml of freshly distilled n-hexane under argon. TMEDA (15 mmol) was added followed by n-BuLi (10 mmol, 1.6 M in hexane) at room temperature. The reaction mixture was refluxed for 3 h. A solution of the corresponding chlorophosphine (10 mmol in 5 ml hexane) was slowly added via syringe. The mixture was further refluxed for 1 h. After cooling to room temperature, degassed water (15 ml) was added and the mixture was stirred to get a clear solution. The aqueous layer was extracted with hexane (2×15 ml) and the combined organic layers were washed with degassed water (15 ml). The solution was dried over $Na_2SO_4$ and concentrated at 45° C. to get a viscous liquid which was recrystallized from methanol or toluene.

EXAMPLE 66

Catalytic Amination of Aryl Chlorides

A 30 mL pressure tube was loaded with $Pd(OAc)_2$ (0.025 mol), the ligand (0.050 mmol), NaOtBu (6.0 mmol) and was purged by argon for 30 minutes. Then, were successively added under argon, toluene (5 mL), the aryl chloride (5 mmol) and the amine (6 mmol). The mixture was stirred under argon at 120° C. for 20 hours. After reaction, it was diluted with diethylether (15 mL) and washed with water (10 mL). After extraction, the organic phase was dried over $MgSO_4$, concentrated under vacuum and the final product was isolated by column chromatography (silicagel, hexane/ethyl acetate 90/10). Alternatively, diethyleneglycol-di-n-butylether or hexadecane was added as internal standard, and quantitative analysis was done by gas chromatography.

TABLE 1

Amination of chloro-benzene with aniline using ligands 1 to 10: comparison of the activity.

| Entry | Ligand | Conv. [%][a] | Yield [%][a] | T.O.N. |
|---|---|---|---|---|
| 1 | N-phenyl pyrrole-2-$PPh_2$ | 2 | 1 | 2 |
| 2 | N-phenyl pyrrole-2-$PCy_2$ | 11 | 9 | 18 |
| 3 | N-phenyl pyrrole-2-$PtBu_2$ | 97 | 68 | 136 |
| 4 | N-phenyl pyrrole-2-$PAd_2$ | 77 | 76 | 152 |
| 5 | N-naphthyl pyrrole-2-$PtBu_2$ | 91 | 87 | 174 |
| 6 | N-naphthyl pyrrole-2-$PCy_2$ | 69 | 68 | 136 |
| 7 | N-(2-methoxyphenyl) pyrrole-2-$PCy_2$ | 62 | 62 | 124 |
| 8 | N-phenyl indole-2-$PCy_2$ | 13 | 9 | 18 |
| 9 | N-phenyl indole-2-$PtBu_2$ | 94 | 87 | 174 |
| 10 | N-phenyl indole-2-$PAd_2$ | 49 | 46 | 92 |

5 mmol aryl chloride, 6 mmol amine, 6 mmol NaOtBu, 0.5 mol % $Pd(OAc)_2$, 1 mol % ligand, 5 mL toluene, 48 h, 120° C.
[a]Average of 2 runs, determined by GC using diethyleneglycol di-n-butyl ether as internal standard.

TABLE 2

Various aminations of chloro-benzene using ligand 9.

| Entry | Aryl chloride | Amine | Product | Conv. [%][a] | Yield [%][a] |
|---|---|---|---|---|---|
| 1 | PhCl | aniline (H2N-Ph) | diphenylamine (Ph-NH-Ph) | 94 | 87 |
| 2[b] | PhCl | diethylamine (HN(Et)2) | N,N-diethylaniline | 81 | 57 |
| 3 | PhCl | morpholine | 4-phenylmorpholine | 100 | 97 |
| 4 | PhCl | n-butylamine (H2N-Bu) | N-butylaniline | 100 | 91 |
| 5 | PhCl | N-methylaniline | N-methyl-N-phenylaniline | 100 | 94 |
| 6[c] | PhCl | diphenylamine | triphenylamine | 100 | 99 |
| 7 | PhCl | o-toluidine | N-phenyl-o-toluidine | 100 | 95 |

5 mmol aryl chloride, 6 mmol amine, 6 mmol NaOtBu, 0.5 mol % Pd(OAc)$_2$, 1 mol % ligand, 5 mL toluene, 20 h, 120° C. Reaction time has not been minimized.
[a]Average of 2 runs, determined by GC using diethyleneglycol di-n-butyl ether or hexadecane as internal standard.
[b]The reaction was conducted within 48 hours.
[c]Ligand 5 was used (2 equiv/Pd).

TABLE 3

Various aminations of functionalized aryl-chlorides and chloro-pyridines using ligand 9.

| Entry | Aryl-chloride | Amine | Product | Conv. [%][a] | Yield [%][a] |
|---|---|---|---|---|---|
| 1 | 2-chlorotoluene | n-butylamine (H2N-Bu) | 2-methyl-N-butylaniline (NHBu) | 100 | 99 |

TABLE 3-continued
Various aminations of functionalized aryl-chlorides and chloro-pyridines using ligand 9.
| Entry | Aryl-chloride | Amine | Product | Conv. [%][a] | Yield [%][a] |
|---|---|---|---|---|---|
| 2 | 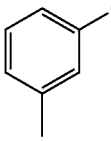 | 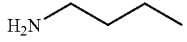 | 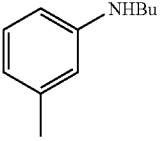 | 100 | 88 |
| 3 | 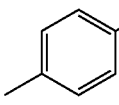 | 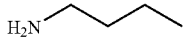 | 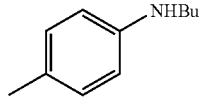 | 100 | 95 |
| 4 | 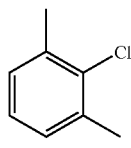 | 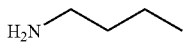 | 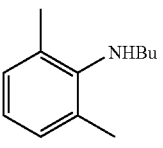 | 100 | 95 |
| 5 | 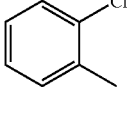 | 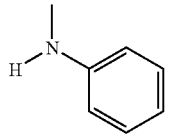 | 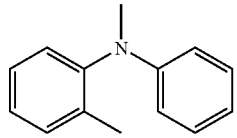 | 100 | 92 |
| 6 | 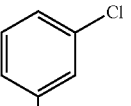 | 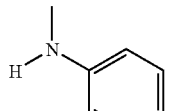 | 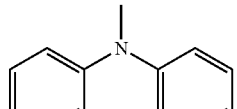 | 100 | 95 |
| 7 | 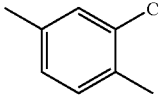 | 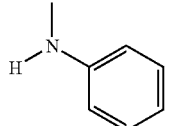 | 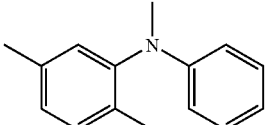 | 100 | 91 |
| 8[b] | 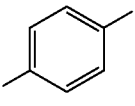 | 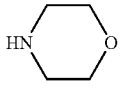 | 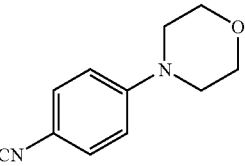 | 100 | 75 |
| 9 | 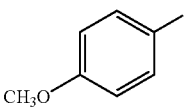 | 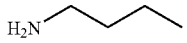 | 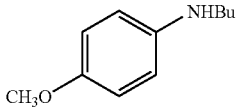 | 100 | 88 |
| 10 | 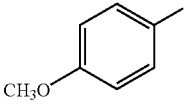 | 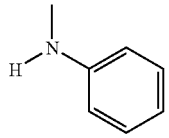 | 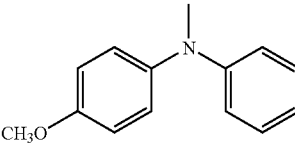 | 100 | 90 |

TABLE 3-continued

Various aminations of functionalized aryl-chlorides and chloro-pyridines using ligand 9.

| Entry | Aryl-chloride | Amine | Product | Conv. [%][a] | Yield [%][a] |
|---|---|---|---|---|---|
| 11 | 4-Cl-C6H4-CF3 | PhNHMe | 4-CF3-C6H4-N(Me)Ph | 100 | 97 |
| 12 | 3-Cl-C6H4-CF3 | PhNHMe | 3-CF3-C6H4-N(Me)Ph | 100 | 98 |
| 13 | 2,4-difluoro-chlorobenzene | PhNHMe | 2,4-difluoro-C6H3-N(Me)Ph | 100 | 98 |
| 14 | 2-chloropyridine | morpholine | 2-morpholinopyridine | 100 | 60/Lig. 9<br>99/Lig. 8 |
| 15[b] | 2-chloropyridine | o-toluidine | N-(o-tolyl)-2-aminopyridine | 100 | 92 |
| 16 | 2-chloropyridine | 1-benzylpiperazine | 2-(4-benzylpiperazin-1-yl)pyridine | 100 | 77/Lig. 9<br>99/Lig. 8 |
| 17 | 2-chloro-6-methoxypyridine | morpholine | 2-methoxy-6-morpholinopyridine | 100 | 99/Lig. 8 |
| 18 | 2-chloroquinoline | 1-benzylpiperazine | 2-(4-benzylpiperazin-1-yl)quinoline | 100 | 90 |
| 19[b] | 3-chloropyridine | PhNHMe | 3-(N-methyl-N-phenylamino)pyridine | 100 | 99 |

5 mmol aryl chloride, 6 mmol amine, 6 mmol NaOtBu, 0.5 mol % Pd(OAc)$_2$, 1 mol % ligand, 5 mL toluene, 20 h, 120° C. Reaction time has not been minimized.
[a]Average of 2 runs, determined by GC using diethyleneglycol di-n-butyl ether or hexadecane as internal standard.
[b]1 mol % Pd(OAc)$_2$, 2 mol % ligand.

TABLE 4

Amination of 3-chloro-toluene with N-methyl-aniline: variations of temperature and catalyst loading

| Entry | mol % Pd | L/Pd | Temp. [° C.] | Conv. [%][a] | Yield [%][a] | TON |
|---|---|---|---|---|---|---|
| 1 | 0.5 | 2 | 120 | 100 | 95 | 190 |
| 2 | 0.5 | 2 | 100 | 100 | 92 | 184 |
| 3 | 0.5 | 2 | 80 | 100 | 90 | 180 |
| 4 | 0.5 | 2 | 60 | 100 | 89 | 178 |
| 5 | 0.5 | 2 | 40 | 100 | 90 | 180 |
| 6 | 0.25 | 2 | 120 | 100 | 91 | 364 |
| 7 | 0.1 | 2 | 120 | 98 | 86 | 860 |
| 8 | 0.05 | 2 | 120 | 83 | 73 | 1460 |
| 9 | 0.025 | 2 | 120 | 70 | 62 | 2480 |
| 10 | 0.025 | 10 | 120 | 78 | 67 | 2680 |
| 11 | 0.01 | 2 | 120 | 24 | 23 | 2300 |
| 12 | 0.01 | 25 | 120 | 39 | 33 | 3300 |
| 13 | 0.01 | 50 | 120 | 45 | 37 | 3700 |

5 mmol aryl chloride, 6 mmol amine, 6 mmol NaOtBu, 5 mL toluene, 20 h. Reaction time has not been minimized.
[a]Average of 2 runs, determined by GC using diethyleneglycol di-n-butyl ether as internal standard.

TABLE 5

Various aminations of aryl-chlorides at low temperature using ligand 9.

| Entry | Aryl-chloride | Amine | Product | Temp. [° C.] | Yield [%][a] |
|---|---|---|---|---|---|
| 1[b] | 4-CF$_3$-C$_6$H$_4$-Cl | PhNHMe | 4-CF$_3$-C$_6$H$_4$-N(Me)Ph | 25 | 97 |
| 2[b] | 3-CF$_3$-C$_6$H$_4$-Cl | PhNHMe | 3-CF$_3$-C$_6$H$_4$-N(Me)Ph | 25 | 98 |
| 3 | 4-CH$_3$O-C$_6$H$_4$-Cl | PhNHMe | 4-CH$_3$O-C$_6$H$_4$-N(Me)Ph | 60 | 91 |
| 4 | 2,4-F$_2$-C$_6$H$_3$-Cl | PhNHMe | 2,4-F$_2$-C$_6$H$_3$-N(Me)Ph | 60 | 98 |
| 5 | C$_6$H$_5$-Cl | morpholine | C$_6$H$_5$-morpholine | 60 | 97 |
| 6 | 2,5-Me$_2$-C$_6$H$_3$-Cl | PhNHMe | 2,5-Me$_2$-C$_6$H$_3$-N(Me)Ph | 60 | 91 |

5 mmol aryl chloride, 6 mmol amine, 6 mmol NaOtBu, 0.5 mol % Pd(OAc)$_2$, 1 mol % ligand, 5 mL toluene, 20 h. Reaction time has not been minimized.
[a]Average of 2 runs, determined by GC using diethyleneglycol di-n-butyl ether or hexadecane as internal standard.
[b]1 mol % Pd(OAc)$_2$, 2 mol % ligand.

The invention claimed is:
1. A phosphane ligand of formula (I)

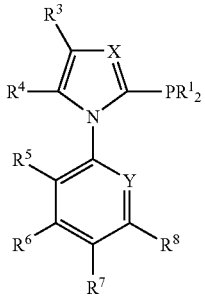

(I)

wherein
X independently of Y represents a nitrogen atom or a C-R² group and
Y independently of X represents a nitrogen atom or a C-R⁹ group,
R¹ for each of the two R¹ groups independently of the other represents a radical selected from the group consisting of
a $C_1$-$C_{24}$-alkyl radical,
a $C_3$-$C_{20}$-cycloalkyl radical,
which comprises monocyclic, bicyclic, and tricyclic cycloalkyl radicals,
a $C_5$-$C_{14}$-aryl radical,
which comprises a phenyl radical, a naplithyl radical, and a fluorenyl radical, with the proviso that if one R¹ is a non-substituted phenyl, the second R¹ cannot be a non-substituted phenyl,
and a $C_2$-$C_{13}$-heteroaryl radical,
wherein the heteroatoms comprise nitrogen, oxygen, sulfur, or a combination thereof and wherein the number of heteroatoms is from 1 to 2,
wherein the two radicals R¹ may be linked to one another,
wherein the above-mentioned radicals R¹ may each be mono- or poly-substituted independently of one another by substituents selected from the group consisting of hydrogen, a $C_1$-$C_{20}$-alkyl radical, a $C_2$-$C_{20}$-alkenyl radical, a $C_3$-$C_8$-cycloalkyl radical, a $C_2$-$C_9$-hetero-alkyl radical, a $C_5$-$C_{10}$-aryl radical, a $C_2$-$C_9$-heteroaryl radical,
wherein the heteroatoms comprise nitrogen, oxygen, sulfur, or a combination thereof
and wherein the number of hetero atoms is from 1 to 4,
a $C_1$-$C_{20}$-alkoxy radical, a $C_1$-$C_{10}$-haloalkyl radical, a hydroxyl radical, a NH—($C_1$-$C_{20}$-alkyl) radical, a NH—($C_5$-$C_{10}$-aryl) radical, a N ($C_1$-$C_{20}$-alkyl)₂ radical, a N ($C_1$-$C_{20}$-alkyl) ($C_5$-$C_{10}$-aryl) radical, a N($C_5$-$C_{10}$-aryl)₂ radical, a N($C_1$-$C_{20}$-alkyl/$C_5$-$C_{10}$-aryl₃)₃⁺ radical, a NH—CO—$C_1$-$C_{20}$-alkyl radical, a NH—CO—$C_5$-$C_{10}$-aryl radical, a COOH radical, a COOQ' radical, a $C_1$-$C_6$-acyloxy radical, a sulfinato radical, a —SO₃H radical, a SO₃Q" radical and a tri-$C_1$-$C_6$-alkylsilyl radical,
wherein Q' represents either a monovalent cation or a $C_1$-$C_8$-alkyl radical and Q" represents either a monovalent cation, a $C_1$-$C_{20}$-alkyl radical, or a $C_5$-$C_{10}$-aryl radical,
wherein two of the mentioned substituents may be bridged with one another, R₂-R₉ independently represent hydrogen, an alkyl radical, an alkenyl radical, a cycloalkyl radical, an aromatic or heteroaromatic aryl radical, an O-alkyl radical, an NH-alkyl radical, an N-(alkyl)₂ radical, an O-(aryl) radical, an NH-(aryl) radical, an N-(alkyl)(aryl) radical, an O—CO-alkyl radical, a O—CO-aryl radical, a F, a Si(alkyl)₃ radical, a CF₃ radical, a CN radical, a CO₂H radical, a COH radical, an SO₃H radical, a CONH₂ radical, an CONH(alkyl) radical, a CON(alkyl)₂ radical, an SO₂(alkyl) radical, a SO(alkyl) radical, a SO(aryl) radical, a SO₂(aryl) radical, a SO₃(alkyl) radical, a SO₃(aryl) radical, an S-alkyl radical, an S-aryl radical, a NH—CO(alkyl) radical, a C₂(alkyl) radical, a CONH₂ radical, a CO(alkyl) radical, a NHCOH radical, a NHCO₂(alkyl) radical, a CO(aryl) radical, or a C₂(aryl) radical,
wherein two or more adjacent radicals, each independently of the other(s), may also be linked to one another so that a condensed ring system is present and
wherein in R² to R⁹
an alkyl radical comprises a hydrocarbon radical comprising from 1 to 20 carbon atoms which may be linear or branched, an alkenyl radical represents a mono- or poly-unsaturated hydrocarbon radical comprising from 2 to 20 carbon atoms which may in be linear or branched, a cycloalkyl radical comprises a hydrocarbon comprising from 3 to 20 carbon atoms, an aryl radical comprises a 5- to 14-membered aromatic radical, wherein from one to four carbon atoms in the aryl radical may be replaced by hetero atoms wherein the heteroatoms are nitrogen, sulfur, and oxygen so that a 5- to 14-membered heteroaromatic radical is present, wherein the radicals R² to R⁹ may also carry further substituents as defined for R¹.

2. The phosphane ligand according to claim 1, wherein X is a CR² group and Y is a CR⁹ group.

3. The phosphane ligand of claim 1, wherein X is nitrogen and Y is a CR⁹ group.

4. The phosphane ligand of claim 1, which comprises at least one radical R¹ selected from the group consisting of a phenyl radical, a $C_1$-$C_{10}$-alkyl radical, a cyclopentyl radical, a cyclohexyl radical, a cyclo-heptyl radical, a 1-adamantyl radical, a 2-adamantyl radical, a 5H-dibenzo-phospholyl radical, a 9-phosphabicyclo[3.3.1]nonanyl radical, and a 9-phospha-bicyclo[4.2.1]nonanyl radicals,
wherein if one R¹ is a non-substituted phenyl, the second R¹ cannot be a non-substituted phenyl.

5. The phosphane ligand of claim 1, wherein the ligand radicals R² to R⁹ are selected from the group consisting of hydrogen, a $C_1$-$C_{10}$-alkyl radical, a $C_2$-$C_{10}$ alkenyl radical, a $C_1$-$C_{10}$-haloalkyl radical, a $C_3$-$C_8$-cycloalkyl radical, a $C_6$-$C_{10}$-aryl radical, and a $C_2$-$C_6$-heteroaryl radical, wherein from 1 to 3 nitrogen atoms an oxygen atom, a sulfur atom, or a combination thereof may be present and wherein two adjacent radicals R² to R⁹ may be bridged with one another.

6. A catalyst comprising at least one metal of sub-group VIII and at least one phosphane ligand of claim 1.

7. The catalyst of claim 6, wherein the catalyst comprises at least one selected from the group consisting of palladium, nickel, platinum, rhodium, iridium, ruthenium a cobalt atom, and a cobalt ion.

8. The catalyst according to claim 6, wherein the catalyst is a mono-, di-, tri- or tetra-phosphane ligand complex of the metal.

9. A catalytic process for converting a chloro or bromo aromatic or vinyl compound to a coupling product comprising:

preparing a reaction mixture comprising a bromo- or chloro aromatic compound or a bromo- or chloro vinyl compound and a second reactant to be coupled to the bromo- or chloro aromatic compound or the bromo- or chloro vinyl compound, and reacting the bromo- or chloro aromatic compound or the bromo- or chloro vinyl compound with the second reactant to be coupled to the bromo- or chloro aromatic compound or the bromo- or chloro vinyl compound in the presence of the catalyst of claim 6 to form the coupling product wherein the catalyst is either fed to the reaction mixture in the form of a complex compound or the catalyst is produced in situ in the reaction mixture.

10. The process of claim 9, wherein the the reaction of the bromo- or chloro aromatic compound or the bromo- or chloro vinyl compound with the second reactant to be coupled to the bromo- or chloro aromatic compound or the bromo- or chloro vinyl compound is at a temperature in a range of from 20 to 200° C.

11. The process of claim 9 wherein a molar ratio of metal to phosphane ligand in the catalyst is from 1:1 to 1:1000.

12. The process according to claim 11, wherein the ratio of metal to ligand is from 1:1 to 1:100.

13. The process of claim 9 wherein a ratio of the metal relative to the bromo- or chloro aromatic compound or the bromo- or chloro vinyl compound is from 5 mol. % to 0.001 mol. %.

14. The ligands of claim 2, wherein the ligands carry at least one radical $R^1$ selected from the group consisting of a phenyl radical, a $C_1$-$C_{10}$-alkyl radical, a cyclopentyl radical, a cyclohexyl radical, a cyclo-heptyl radical, a 1-adamantyl radical, a 2-adamantyl radical, a 5 H-dibenzo-phospholyl radical, a 9-phosphabicyclo [3.3.1]nonanyl radical, and a 9-phospha-bicyclo[4.2.1]nonanyl radical, with the proviso that if one $R^1$ is a non-substituted phenyl, the second $R^1$ cannot be a non-substituted phenyl.

15. The ligands of claim 3, wherein the ligands carry at least one radical $R^1$ selected from the group consisting of a phenyl radical, a $C_1$-$C_{10}$-alkyl radical, a cyclopentyl radical, a cyclohexyl radical, a cyclo-heptyl radical, a 1-adamantyl radical, a 2-adamantyl radical, a 5 H-dibenzo-phospholyl radical, a 9-phosphabicyclo [3.3.1]nonanyl radical, and a 9-phospha-bicyclo[4.2.1]nonanyl radical, with the proviso that if one $R^1$ is a non-substituted phenyl, the second $R^1$ cannot be a non-substituted phenyl.

16. The ligands of claim 2, wherein the ligand radicals $R^2$ to $R^9$ are selected from the group consisting of hydrogen, a $C_1$-$C_{10}$-alkyl radical, a $C_2$-$C_{10}$ alkenyl radical, a $C_1$-$C_{10}$-haloalkyl radical, a $C_3$-$C_8$-cycloalkyl radical, a $C_6$-$C_{10}$-aryl radical, and a $C_2$-$C_6$-heteroaryl radical, wherein from 1 to 3 nitrogen atoms an oxygen atom, a sulfur atom, or a combination thereof may be present and wherein two adjacent radicals $R^2$ to $R^9$ may be bridged with one another.

17. The ligands of claim 3, wherein the ligand radicals $R^2$ to $R^9$ are selected from the group consisting of hydrogen, a $C_1$-$C_{10}$-alkyl radical, a $C_2$-$C_{10}$ alkenyl radical, a $C_1$-$C_{10}$-haloalkyl radical, a $C_3$-$C_8$-cycloalkyl radical, a $C_6$-$C_{10}$-aryl radical, and a $C_2$-$C_6$-heteroaryl radical, wherein from 1 to 3 nitrogen atoms an oxygen atom, a sulfur atom, or a combination thereof may be present and wherein two adjacent radicals $R^2$ to $R^9$ may be bridged with one another.

18. The ligands of claim 4, wherein the ligand radicals $R^2$ to $R^9$ are selected from the group consisting of hydrogen, a $C_1$-$C_{10}$-alkyl radical, a $C_2$-$C_{10}$ alkenyl radical, a $C_1$-$C_{10}$-haloalkyl radical, a $C_3$-$C_8$-cycloalkyl radical, a $C_6$-$C_{10}$-aryl radical, and a $C_2$-$C_6$-heteroaryl radical, wherein from 1 to 3 nitrogen atoms an oxygen atom, a sulfur atom, or a combination thereof may be present and wherein two adjacent radicals $R^2$ $R^9$ may be bridged with one another.

* * * * *